United States Patent
Dhanaraj et al.

(10) Patent No.: US 9,801,910 B2
(45) Date of Patent: Oct. 31, 2017

(54) DECELLULARIZED PLEURAL MATRIX

(71) Applicant: Ethicon, Inc., Somerville, NJ (US)

(72) Inventors: Sridevi Dhanaraj, Raritan, NJ (US); Chandra M. Valmikinathan, Elmwood Park, NJ (US); Charito Buensuceso, Raritan, NJ (US); Agnieszka Seyda, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 569 days.

(21) Appl. No.: 14/215,429

(22) Filed: Mar. 17, 2014

(65) Prior Publication Data

US 2015/0258142 A1   Sep. 17, 2015

(51) Int. Cl.
*C12N 5/00*   (2006.01)
*C12N 5/02*   (2006.01)
*A61K 35/12*  (2015.01)
*A61L 27/36*  (2006.01)

(52) U.S. Cl.
CPC .......... *A61K 35/12* (2013.01); *A61L 27/3633* (2013.01)

(58) Field of Classification Search
None
See application file for complete search history.

(56) References Cited

U.S. PATENT DOCUMENTS

| | | |
|---|---|---|
| 7,179,287 B2 | 2/2007 | Wolfinbarger, Jr. |
| 7,198,855 B2 | 4/2007 | Liebmann-Vinson |
| 7,361,195 B2 | 4/2008 | Schwartz |
| 7,550,152 B2 | 6/2009 | Pandit |
| 7,722,894 B2 | 5/2010 | Wang |
| 7,745,217 B2 | 6/2010 | Patel |
| 7,763,268 B2 | 7/2010 | Chen |
| 7,795,027 B2 | 9/2010 | Hiles |
| 7,931,692 B2 | 4/2011 | Sybert |
| RE42,575 E | 7/2011 | Vacanti |
| 7,985,414 B2 | 7/2011 | Knaack |
| 8,012,205 B2 | 9/2011 | Plouhar |
| 8,043,614 B2 | 10/2011 | Ahlfors |
| 8,076,137 B2 | 12/2011 | McAllister |
| 8,143,042 B2 | 3/2012 | Bettinger |
| 8,192,763 B2 | 6/2012 | Johnson |
| 8,192,835 B2 | 6/2012 | Chi |
| 8,198,087 B2 | 6/2012 | Bayon |
| 8,333,803 B2 | 12/2012 | Park |
| 8,357,172 B2 | 1/2013 | Harper |
| 8,409,625 B2 | 4/2013 | Badylak |
| 8,409,626 B2 | 4/2013 | Daniel |
| 8,415,159 B2 | 4/2013 | Ward |
| 8,460,715 B2 | 6/2013 | Daniel |
| 2002/0086852 A1 | 7/2002 | Cantor |
| 2007/0250177 A1 | 10/2007 | Bilbo |
| 2007/0280985 A1 | 12/2007 | Depaola |
| 2009/0142396 A1* | 6/2009 | Odar ..................... A61L 31/14 424/484 |
| 2010/0030259 A1* | 2/2010 | Pavcnik ............. A61B 17/0057 606/215 |
| 2010/0082113 A1 | 4/2010 | Gingras |
| 2011/0224779 A1* | 9/2011 | Schankereli ........ A61L 27/3604 623/1.24 |
| 2011/0293666 A1* | 12/2011 | Wang .................. A61L 27/3633 424/400 |
| 2013/0053872 A1* | 2/2013 | Hansen ............ A61B 17/12031 606/151 |

FOREIGN PATENT DOCUMENTS

| | | |
|---|---|---|
| WO | WO 99/66967 A1 | 12/1999 |
| WO | WO 2007011644 A2 | 1/2007 |
| WO | WO 2007011644 A3 | 8/2007 |
| WO | WO 2013/120082 A1 | 8/2013 |

OTHER PUBLICATIONS

D.M.Hoganson et al., Preserved extracellular matrix components and retained biological activity in decellularized porcine mesothelium, Biomaterials 31 (2010) 6934-6940.

* cited by examiner

*Primary Examiner* — Chris R Tate
*Assistant Examiner* — Douglas F White

(57) ABSTRACT

The present invention pertains to the development of biologically derived extracellular matrices (ECM) derived from decellularized pleura tissue. Such matrices are useful in many clinical and therapeutic applications, including the repair, reconstruction, sealing, or joining of tissue, tendons, bones, and/or ligaments. In addition, the present invention features methods of making a biologically derived ECM derived from decellularized pleura tissue. The invention further features laminated ECM matrices.

24 Claims, 14 Drawing Sheets
(11 of 14 Drawing Sheet(s) Filed in Color)

1a   1b   1c 2a 2b 2c 3a          3b          3c

DECELLULARIZED PLEURAL MATRIX

BACKGROUND OF THE INVENTION

Biologically derived extracellular matrices (ECM) have been used for tissue repair and regeneration. The two most commonly used matrices, however, which are derived from dermis and the small intestine, have limitations. These tissues being very cellular, well vascularized, and associated with adipose tissue require harsh processing conditions that may damage the native ECM structure. Embodiments of the present invention overcome one or more of these challenges.

BRIEF SUMMARY OF THE INVENTION

The present disclosure provides several exemplary embodiments of the present invention, some of which are discussed below.

In an aspect, the present invention provides a biologically derived extracellular matrix (ECM) having decellularized pleura tissue. In one embodiment, the pleura tissue is of mammalian origin. In another embodiment, the pleura tissue is derived from porcine, bovine, ovine, canine, murine, simian, caprine, equine, avian, or human. In still another embodiment, the matrix is configured as a sheet, a perforated sheet, laminated sheets, strips, pieces, a coil, a cylinder, a weave, a vacuum pressed material, a sponge, a micronized powder, a paste, an injectable gel, a spray, an emulsion, or a coating. The matrices of the present invention can be used to repair, reconstruct, seal, or join nervous tissue, dermal tissue, cardiovascular tissue, pericardial tissue, muscle tissue, bladder tissue, ocular tissue, periodontal tissue, bone, tendons, ligaments, pelvic floor tissue, or abdominal tissue.

In one embodiment, the matrix has a plurality of layers of decellularized pleura tissue. In another embodiment, the matrix has a burst strength of at least 8 N multiplied by the number of layers. In yet another embodiment, the matrix has a tensile strength of at least 2 N multiplied by the number of layers. In still another embodiment the matrix has a thickness of not more than 0.105 mm multiplied by the number of layers.

In one embodiment, the ECM having decellularized pleura tissue is made up of four layers of decellularized pleura tissue and has elasticity which is characterized by a bending modulus of not more than about 363 MPa on average or about 524 MPa including standard deviation and the bending modulus is measured by a 3-point bending test. In another embodiment, the matrix also has a micronized ECM deposited on at least one surface of the ECM, the micronized ECM comprising micro particles made of the decellularized pleura tissue. In this embodiment, a pleura is micronized in a milling machine as known to these skilled art, and then applied onto the decellularized pleura and immobilized or bonded using thermal treatment, compression, or a biocompatible adhesive. In still another embodiment, the matrix has at least one layer of bioabsorbable polymers, wherein said bioabsorbable polymers are collagen, gelatin, chitosan, oxidized cellulose, oxidized regenerated cellulose, lactide-containing copolymers, glycolide containing co-polymers, or combinations thereof.

In an aspect, the present invention provides a method of making a biologically derived ECM according to the embodiments described herein. In one embodiment, the method involves providing a pleura tissue; decellularizing the pleura tissue; and lyophilizing the pleura tissue. In another embodiment, the method involves the additional step of rehydrating the pleura tissue forming a decellularized ECM.

In another embodiment, the method involves providing pleura tissue; decellularizing the pleura tissue; forming a plurality of pleura tissue layers of the decellularized pleura tissue; stacking the plurality of pleura tissue layers on top of each other forming a stack; compressing the stack under vacuum; and lyophilizing the compressed stack. In yet another embodiment, the step of stacking the plurality of pleura tissue layers on top of each other forming a stack is performed with a serosal side of the pleura tissue layers facing up and a basement side of the pleura tissue layers facing down.

In another aspect, the present invention provides a biologically derived ECM having decellularized pleura tissue prepared according to the embodiments described herein.

BRIEF DESCRIPTION OF THE DRAWINGS

The patent or application file contains at least one drawing executed in color. Copies of this patent with color drawing(s) will be provided by the Patent and Trademark Office upon request and payment of the necessary fee.

FIGS. 2a, 2b, and 2c illustrate pleura tissue, and FIGS. 3a, 3b, and 3c illustrate peritoneum tissue.

DETAILED DESCRIPTION OF THE INVENTION

Figure 1:
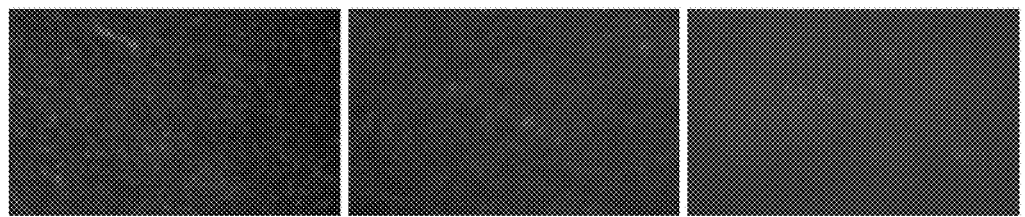
FIG. 1a illustrates stained pleura tissue before a hypotonic wash.
FIG. 1b illustrates stained pleura tissue after a hypotonic wash.
FIG. 1c illustrates stained pleura tissue after treatment DNase.

Reference will now be made in detail to the various embodiments of the present disclosure. This invention pertains to a biologically derived ECM comprising decellularized pleura tissue. One of the reasons for scarcity of pleura-derived decellularized biomaterials is the difficulty in separating the pleura attached to the chest cavity.

The decellularized ECM compositions derived from pleural tissue can be used for reconstruction, repair, and replacement, sealing leaks, and joining structures. In one embodiment, the ECM comprises a plurality of layers of decellularized pleura tissue.

Pleural membrane encloses the lungs and consists of a layer of mesothelial cells resting on connective tissue beneath which is a stroma of collagenous tissue with elastic fibers. Decellularized ECM from pleura is distinct from other ECM by the nature of its function and has the advantage over dermal and submucosal derived materials because of its low cellularity, low adiposity, and low vascularity. It also does not contain any of the glandular elements seen in the submucosal and dermal tissue. Being derived from the thoracic cavity, the pleural membrane has lower bioburden and can therefore be subject to less harsh processing methodologies. (Bioburden is referring to bacterial content, and since the chest cavity has less exposure to bacteria than dermis (derived from skin) and SIS (which is derived from the intestine). It is a strong matrix and therefore does not require additional cross linking. The high content of elastin in the membrane is beneficial as it accommodates the expansion and contraction of the lung during respiration.

The pleural membrane ECM can be of mammalian origin and can be further obtained from a selected group consisting of porcine, bovine, ovine, canine, murine, simian, caprine, equine, avian, and human. In one embodiment, the pleura tissue of the ECM is of mammalian origin. In another embodiment, the pleural membrane is porcine derived.

The invention also provides a method for preparing a graft using a gentle processing method to preserve the native ECM structure and composition. The method comprises obtaining the pleural membrane from a desired source and treating the membrane with a series of hypotonic and hypertonic salt solutions to disrupt the cells and cell membranes. The membranes are then treated with a unique combination of detergent and if required a basic solution to further disrupt cells and solubilize DNA and other nucleic acid. The pleural membrane can be rinsed to remove any residual detergent and base solutions. It can then be stored for use as frozen, as a freeze dried material, in aqueous solution or terminal sterilized by e-beam or gamma sterilization.

The pleural derived ECM can be shaped and reconfigured for use as a sheet, perforated sheet, laminated sheets, strips, pieces, a coil, a cylinder, a weave, a vacuum pressed material, a sponge, a micronized powder, a paste, an injectable gel, a spray, an emulsion, or a coating. Mechanical composite matrices can be produced by stacking layers of ECM on top of each other. Pleural ECM can be further deposited with a second micronized ECM on the top. Composite matrices with other synthetic bioabsorbable polymers can also be achieved.

The various configurations of material described above can be applied to the repair, reconstruction, sealing leaks, and joining tissues for a variety of tissue including nervous tissue, dermal tissue, cardiovascular tissue, pericardial tissue, muscle tissue, bladder tissue, ocular tissue, periodontal tissue, bone, tendons, ligaments, pelvic floor repair, treatment of incontinence, and abdominal wall repair. When implanted into the repair site, the pleural ECM can be remodeled and integrated into the repair tissue.

In one embodiment, the pleural derived ECM has a burst strength of at least 8 N multiplied by the number of layers. In another embodiment, the inventive ECM has a tensile strength of at least 2 N multiplied by the number of layers. In yet another embodiment, the pleural derived ECM has a thickness of not more than 0.105 mm multiplied by the number of layers. In still another embodiment, the inventive ECM comprises four layers of the decellularized pleura tissue and has elasticity which is characterized by a bending modulus of not more than about 363 MPa on average or not more than about 524 MPa including standard deviation, wherein the bending modulus is measured by a 3-point bending test.

In one embodiment, the pleural derived ECM further comprises a micronized ECM deposited on at least one surface of the ECM, the micronized ECM comprising micro particles made of the decellularized pleura tissue. In another embodiment, the inventive ECM further comprises at least one layer of bioabsorbable polymers, wherein said bioabsorbable polymers are collagen, gelatin, chitosan, oxidized cellulose, oxidized regenerated cellulose, lactide-containing copolymers, glycolide containing co-polymers, or combinations thereof.

The invention also provides a method of making a biologically derived ECM. The method comprises the steps: providing pleura tissue; decellularizing the pleura tissue; lyophilizing the pleura tissue; and forming a matrix from the lyophilized pleura tissue. In another embodiment, the method further comprises the step of rehydrating the pleura tissue forming a decellularized ECM.

Another method of making a biologically derived ECM comprises the steps of: providing a pleura tissue; decellularizing the pleura tissue; drying the pleura tissue forming a dried decellularized pleura tissue; forming a plurality of pleura tissue layers of the dried decellularized pleura tissue; stacking the plurality of pleura tissue layers on top of each other forming a stack; compressing the stack under vacuum; and lyophilizing the compressed stack. In another embodiment, the step of stacking the plurality of pleura tissue layers on top of each other forming a stack is performed with a serosal side of the pleura tissue layers facing up and a basement side of the pleura tissue layers facing down.

The invention also provides biologically derived ECM comprising decellularized pleura tissue prepared according to any of the disclosed methods of making a biologically derived ECM.

The following examples are illustrative of the principles and practice of this invention, although not limited thereto. Numerous additional embodiments within the scope and spirit of the invention will become apparent to those skilled in the art once having the benefit of this disclosure.

EXAMPLE 1

Tissue Procurement and Decellularization

Porcine Pleura (approximately 10 pleura tissue from 5 pigs) was obtained from various animal sources including specific pathogen free farms. Procured pleura was harvested from pigs, mechanically cleaned to remove adherent adipose tissue, rinsed in Phosphate Buffered Saline (PBS) and then shipped on ice by overnight delivery. The methods of mechanical cleaning of tissues are known to these skilled in the art. One method which was used for sample preparation was blunt scraper to remove the adherent tissue. Following receipt of the pleura, samples were rinsed three times in PBS containing 0.1 percent ethylenediaminetetraacetic acid (EDTA) and then stored frozen at −20 degrees Celsius until processed. Pleura tissue was obtained from commercial tissue sources, Tissue Source of Lafayette, Ind., and from Farm to Pharm of Warren, N.J. Pleura tissue from Tissue Sources was from certified pathogen free pig.

The pleura tissue measured approximately 12 inches by 12 inches and was decellularized by thawing at room temperature, and once thawed 4-5 Pleura were placed in a 1 liter Nalgene flask containing DPBS (—Ca, —Mg) and 0.1 percent EDTA. The pleura were washed three times 30 minutes each with changes in DPBS 0.1 percent EDTA. In order to remove cellular components, pleura were then transferred into a new flask containing 10 mM Tris-HCl; pH 8.0; and placed on a rotary shaker with gentle shaking at 4 degrees Celsius for 16 hours. This was followed by treatment of pleura with 1 percent Triton X-100 in 10 mM Tris-HCl; pH 8.0 for 24 h at 37 degrees Celsius. Pleura samples were then transferred to a fresh flask containing 1:1 v/v 20 mM Tris HCl pH 8.0 and DPBS with Ca++ and Mg++; and RNase free DNase for 24 hours. Samples were then washed 2 times 30 minutes each time in PBS. Pleura samples were then treated with 1.0 M sodium chloride (NaCl), for 1 hour at room temperature and followed by additional three washes in PBS. The washing regimen serves to wash out dead cells, cell debris, and residual chemicals used in the previous processing steps. At the end of the processing, samples were disinfected by treatment with 0.15 percent peracetic acid (PAA) in 20 percent ethanol for 20 minutes and followed by 3 30-minute washes in PBS.

Unfixed pleura samples were stained with DAPI to visualize nuclei. FIG. 1a shows the pleura tissue before the hypotonic wash, FIG. 1b shows the pleura tissue after the hypotonic wash, and FIG. 1c shows the pleura tissue after treatment with DNase.

EXAMPLE 2

Pleura and Peritoneum

Figure 2:
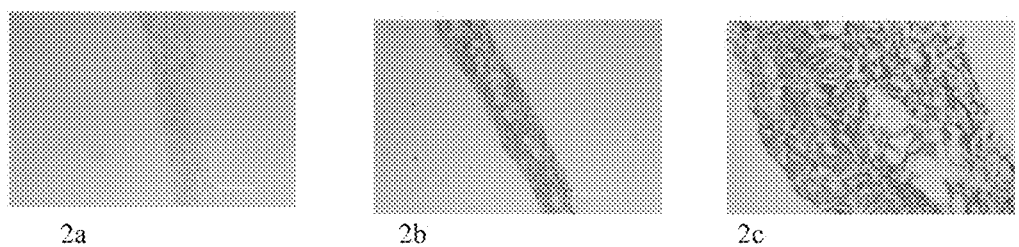
FIGS. 2 and 3 illustrate the difference in thickness, collagen and elastin quantity and distribution between the pleura and peritoneum tissues.
Figure 3:
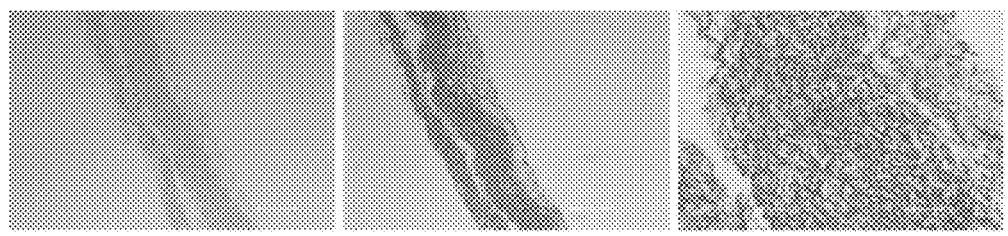

Porcine pleura and peritoneum tissues were obtained from the same animal source. Procured pleura and peritoneum were mechanically cleaned to remove adherent adipose tissue. One of each samples were rinsed three times in PBS containing 0.1 percent ethylenediaminetetraacetic acid (EDTA) and then stored frozen at −20 degrees Celsius until processed. Samples were thawed and approximately a 1 cm×1 cm piece was fixed for histology. FIGS. 2 and 3 illustrate the difference in thickness, collagen and elastin quantity and distribution between the pleura and peritoneum tissues. FIGS. 2a, 2b, and 2c illustrate the pleura tissue, and FIGS. 3a, 3b, and 3c illustrate the peritoneum tissue. FIG. 2a is Hematoxylin eosin stained cross section of pleura and shows the thickness of the pleura. FIGS. 2b and 2c are cross-sections of pleura stained with trichrome and show distribution of collagen and elastin. Collagen is shown as blue and elastin shown as brown. FIG. 3a is Hematoxylin eosin stained cross section of peritoneum and shows the thickness of the peritoneum. FIGS. 3b and 3c are peritoneum stained with trichrome staining and show distribution of collagen and elastin. Collagen is shown as blue and elastin shown as brown.

Equal weights (25 mg) of lyophilized processed pleura and peritoneum tissue were digested with collagenase or papain. 25 mg of Collagenase NB6 was used with constant stirring at 37 degrees Celsius. Papain 100 u in 5 ml was used. All solutions were 5 mL (in sterile PBS). The bulk of the tissue was soluble in papain and collagenase. For pleura, the collagenase insoluble material was 6.4 mg and papain insoluble material was 9.1 mg. For peritoneum, the collagenase insoluble material was 8.4 mg and papain insoluble material was 13.7 mg.

EXAMPLE 3

Lamination of Decellularized Pleura

Pleural membrane by nature of its structure has a sidedness to it with two different surfaces, serosal smooth side and basement membrane (BM) rough side. The inventive multilayered pleural biomatrix of the serosal and basement membrane type construction was constructed from the pleural tissue described in Example 1 by placing the first layer of pleural membrane with the serosal surface facing down on a sterile Teflon sheet and the basement membrane side facing up, a second pleural layer was laid down with the basement membrane side placed over the BM side of the first layer. A third layer was placed such that the serosal side was over the serosal side of the second layer. A fourth layer was placed such that the serosal layer was over the BM side of the third layer resulting in a 4 layer construct with one side of being serosal and the opposite site being basement membrane resulting in a bimodal surface construct, i.e. one side of the construct had BM exposed and another had serosal side exposed. A second sterile Teflon sheet was placed over the construct. The entire construct was then placed between two sterile paper towels and in between two stainless steel platens. The construct was then laminated under vacuum (22 inches mercury) and with pressure (20000 lb) applied simultaneously for 6 hours at room temperature.

The inventive multilayered pleural biomatrix of the basement membrane-basement membrane type construction was constructed in a similar manner as above, but the top and bottom sides of the inventive 4 layer construct are the same: either both serosal or both basement membrane. (In another aspect, it is also contemplated that the multi-layered tissue construct greater than 4 layers can be created.)

In another embodiment, pleura matrix was laminated with synthetic mesh positioned in-between two or more pleura layers. To assemble the implant, 2 layers of pleural membrane were placed on each other while ensuring no air bubbles were trapped between the two. A knitted synthetic mesh (polypropylene) was placed centrally on top two pleura layers and overlaid with two additional pleural membranes. The construct was then laminated by placing it under pressure and vacuum as described above, forming a composite laminate.

Figure 9A:
FIG. 9a illustrates the inventive decellularized pleura (not laminated) constructed for vascular or neural applications, the serosal side facing the mandrel so as to provide a low adherent inner surface for the construct.
Figure 9B:
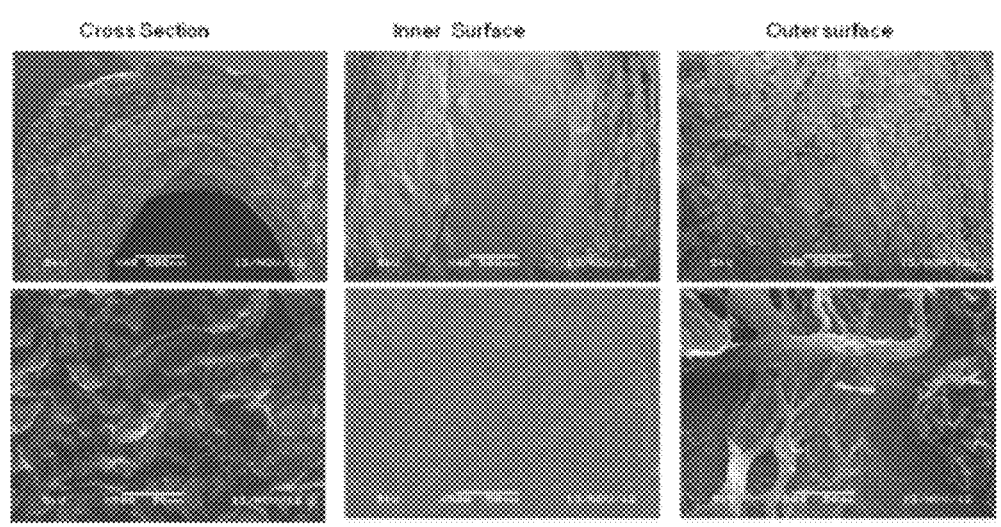
FIG. 9b is an SEM image of the inventive decellularized pleura (not laminated) constructed into a tubular construct showing a well formed tubular construct with a smooth inner surface and a rough exterior surface.

(In alternative embodiments, it is contemplated that pleural membrane layers may also be sutured together to achieve a laminate structure. The inventive laminate may also be achieved through casting and/or crosslinking an aqueous slurry of pulverized or micronized pleural membrane onto a pleura membrane followed by placing another membrane over that. This forms micronized powder of pleura encapsulated between pleura layers construct. Subsequent lyophilization of this construct would use the micronized/pulverized material as a penetrating and bridging agent. The micronized/pulverized pleural membrane may be obtained by decellularizing and lyophilizing the pleural tissue first. The lyophilized pleural membrane would then mechanically pulverized or micronized using any type of milling or mincing devices and then suspended in aqueous solution to form a slurry.)

EXAMPLE 4

Construct Lyophilization and Rehydration

Constructs as described above in Example 3 were placed in a lyophilizer under vacuum and lyophilized. The laminated pleura constructs were dried by the following program: the lyophilization shelf temperature was ramped to minus forty (40) degrees Celsius, and held for 60 minutes, with vacuum set to 500 mT. The shelf temperature was then ramped to minus twenty-five (25) degrees Celsius, and held for 4 hours with vacuum set to 100 mT. The temperature was then ramped to a shelf temperature of minus twenty (20) degrees Celsius, and held for 9 hours with vacuum set to 50 mT. The temperature was then ramped to a shelf temperature of minus ten (10) degrees Celsius and held for 4 hours with vacuum set to 50 mT. The temperature was then ramped to a shelf temperature of minus five (5) degrees Celsius and held for 2 hours with vacuum set to 50 mT. The temperature was then ramped to a shelf temperature of zero (0) degrees Celsius and held for 90 minutes with vacuum set to 50 mT. The temperature was then ramped to a shelf temperature of ten (10) degrees Celsius and held for 90 minutes with vacuum set to 50 mT. The temperature was then ramped to a shelf temperature of twenty (20) degrees Celsius and held for 60 minutes with vacuum set to 50 mT.

Following drying, the laminated pleura constructs were stored at above freezing temperatures, optimally four (4) degrees Celsius in a light protected environment. Prior to use, the constructs were removed and rehydrated by immersion in a normal saline solution at twenty (20) degrees to thirty-seven (37) degrees Celsius for about 2 minutes.

EXAMPLE 5

Scanning Electron Microscopy (SEM) of Laminated Lyophilized Construct

SEM was conducted on samples of the laminated and lyophilized pleural constructs to confirm the sidedness of the matrix and to assess the effect of lamination and lyophilization on the matrices. Samples were analyzed by SEM. Also included were commercially available 10-layer laminate of small intestinal submucosa (SIS) and porcine dermis for comparison.

The SEM images are shown in FIGS. 5*a*-5*c*, showing both top and bottom views, and cross-sections. FIG. 5*a* shows the distinct sidedness (difference in surface characteristics of the top and bottom surfaces) of the inventive pleural serosal-basement membrane type construct. The SIS construct, FIG. 5*b*, showed no difference in surface (no sidedness) apart from the superficial impression attribute probably imparted during compression. Also the dermal matrix, FIG. 5*c*, showed no difference in the two sides (no sidedness).

Cross sectional images by SEM show the 4 layers of laminated lyophilized construct (FIG. 5*a*). Surprisingly, the layers are not as distinct as in the SIS specimen (FIG. 5*b*), indicating an amalgamation of the 4 layers. Also interconnectivity was noted between the layers in the pleural construct. SIS showed the 10 distinct layers and no amalgamation between the layers (FIG. 5*b*). Advantageously, the inventive pleural matrix showed porosity while the SIS and dermal construct are a dense material with little porosity (FIGS. 5*b* and 5*c*, respectively).

EXAMPLE 6

Histology of Laminated Lyophilized Construct

The inventive laminated and lyophilized pleural constructs were fixed in 10 percent neutral buffered formalin for 24 hours, rinsed, and transported in sterile PBS (phosphate buffer saline) for histological assessment. Samples were paraffin embedded, processed, and then stained with Hematoxylin and Eosin (H&E), Masson's Trichrome, Verhoeffs Van Gieson (EVG), and Alcian blue staining, as known in the art. Referring to FIG. 6, H&E and Masson's Trichrome staining confirmed the effectiveness of the decellularization protocol, as no cells or cell fragments could be visualized in any regions of the processed matrix. Further, the overall structure of the ECM appeared to be well-preserved following processing. EVG staining confirmed the preservation of elastin that confers unique properties for the matrix. In addition, the gentle nature of the processing was evident from the retention of the Alcian blue staining for proteoglycans.

Surprisingly, as confirmed by the SEM imaging, there is a full amalgamation of the 4 layers in the inventive construct which is also combined with a unique open matrix structure of the construct.

EXAMPLE 7

Constructing Inventive Laminate Constructs Into Implantable Forms

Laminated and lyophilized pleural constructs can be further processed for specific applications. The pleural matrix can be rendered porous to allow for fluid transport. The size, shape, organization, and density of the pores may vary and may be created using mechanical means or controlled laser micromachining. Pores may also be created in the non-lyophilized laminate and lyophilized later.

According to one embodiment, laminated pleural constructs were processed through a Brennen Tissue Mesher (Brennen Medical, St. Paul, Minn.), to obtain a meshed biomatrix. Referring to FIG. 7, a four layer Laminated and lyophilized pleural construct was processed through the Brennen Tissue Mesher resulting in a meshed pleura matrix.

The laminated pleural construct can also be texturized to enhance the attachment characteristics of one or both surfaces depending on the application. Referring to FIG. 8, a four layer laminated and lyophilized pleural construct was processed by positioning between two stainless steel surfaces with blunt serrations and compressing, resulting in a texturized pleura matrix shown.

The decellularized pleura (not laminated) can also be processed into tubular constructs. In one embodiment, decellularized pleura sheet was wrapped over on itself several times, forming a tubular shape. A stainless steel mandrel of 2 mm diameter was used and was covered with sterile medical grade Teflon tape with an overhang. The Teflon tape provides a non-adherent surface to facilitate easy removal of the construct once formed. The decellularized pleura was wrapped tightly around the mandrel several times. This can be tailored based on the needed thickness and strength. To make the construct for vascular or neural applications the serosal side is facing the mandrel so as to provide a low adherent inner surface for the construct (FIG. 9a). The tubular construct was then lyophilized under vacuum following the method described in Example 4. Following lyophilization the construct was removed by pulling on the Teflon overhang to release the construct. Referring to FIG. 9b, SEM images show a well formed tubular construct with a smooth inner surface and a rough exterior surface.

Figure 9C:
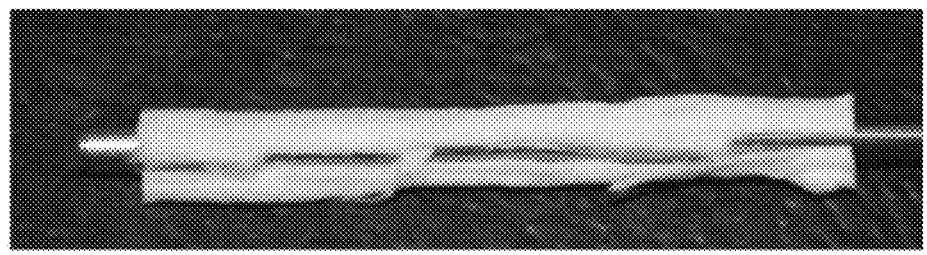
FIG. 9c illustrates an inventive decellularized pleura (not laminated) constructed to be used as an external stent in cases where damaged or diseased blood vessels or auto graft vessels require exterior support.

The inventive tubular pleural construct may be used as an external stent in cases where damaged or diseased blood vessels or auto graft vessels require exterior support. In this case, the tubular construct is made as described above without an overlap such that it can serve as a wrap for a vessel or nerve, as shown in FIG. 9c.

EXAMPLE 8

Cell Seeding on Pleural Matrix

The ability of the inventive pleura biomatrix to support cell attachment and proliferation was evaluated in cell seeding experiments. To prepare the pleura biomatrix for the cell seeding experiments, 10 mm biopsy punches of the pleura both unprocessed and after decellularization were rinsed in PBS containing antibiotic, antimycotic for 20 minutes, 3 changes to render them clean for cell culture.

Each punch was placed in a 24 well low cluster dish. Porcine dermal fibroblasts (Passage 2) were seeded on the pleural biomatrix on the basement membrane side with 60,000 cells per 10 mm punch. Cells were seeded in 60 microliters of complete growth medium to promote cell attachment. Cells were allowed to attach for 30 minute before the culture wells were fed with 1 mL of complete growth medium (37 degrees Celsius, 5 percent $CO_2$).

Figure 10:
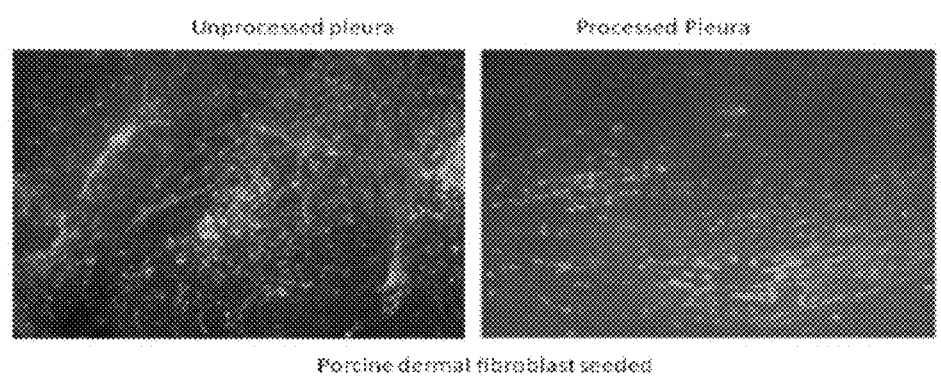
FIG. 10 illustrates a micrograph of fibroblasts seeded on pleura matrix with live/dead staining (Molecular Probes). Live cells stained fluorescent green.

The culture medium was changed every 2 to 3 days and after 1 week in culture, the scaffolds were removed and visualized by live/dead staining (Molecular Probes). Referring to FIG. 10, a micrograph of fibroblasts seeded a on pleura matrix with live/dead staining (Molecular Probes) is shown, whereby live cells stain fluorescent green. The data indicates that fibroblasts seeded on the inventive pleura matrix were viable, making the matrix suitable for implantations.

EXAMPLE 9

Mechanical Properties of Pleura Tissue Biomatrix

Pleural matrix made according to the present invention (Example 4), using pleura derived from the pathogen free farm, was investigated for their thickness and mechanical strength, both tensile testing and bending. For mechanical testing, 4-layered laminate matrices were tested using an Instron 5544 (TJ-41), 100-lb load cell (LC-147). Matrix rectangles made of the inventive multilayered pleural biomatrix of the serosal and basement membrane type construction as described in Example 3, measuring 6×1 cm were tested for tensile strength, both wet and dry (GL=2 cm, Crosshead speed=8 cm/min). At least six (6) samples were utilized. The Bending modulus was determined by a 3 point bending test. Samples were evaluated dry. Suture pull out testing was also performed. The results demonstrated that the pleural matrix have good mechanical properties that can be tailored based on the specific application.

Peritoneum obtained from the same source was processed similarly and evaluated for tensile strength. A commercially available Porcine SIS 10 layer matrix was also evaluated for comparison. Note that the Pleural matrix is more elastic and flexible than the SIS matrix Table 1: Pleural Matrix Thickness and Mechanical Strength Material assessed. Pleura laminates were made from two different sources as described previously. For comparison peritoneum laminates were made from the same source. Comparisons were also made against a 10-layer SIS matrix and a porcine dermal matrix. Thickness was measured at multiple sites using the federal height gauge.

TABLE 2

Thickness of matrices.

| Matrix (porcine) | Thickness (mm) |
| --- | --- |
| Pleura 4-layer laminate Source 1(dry) | 0.18 ± 0.01 |
| Pleura 8-layer laminate Source 1(dry) | 0.56 ± 0.03; |
| Pleura 4-layer laminate Source 2(dry) | 0.42 ± 0.07 |
| Peritoneum 4 layer laminate Source 2(dry) | 0.57 ± 0.08 |
| SIS 10-Layer laminate(dry) | 0.15 ± 0.01 |
| Dermal matrix (wet) | 1.08 ± 0.13 |

As can be seen from Table 2, the inventive matrix had achieved easy to handle and easy to apply thickness, which is not exceeding 0.105 mm or less multiplied by the number of layers.

Tensile Strength and Modulus. Tensile strength assesses the force required to elongate and eventually break the material. Matrix rectangles measuring 6×1 cm were tested for tensile strength in wet and dry conditions. Wet samples were hydrated in saline prior to assessment. Tensile Strength is the force at which material breaks into two pieces under tensile load. Tensile Modulus represents how strong a material is in relating to resistance to deformation under tensile load.

TABLE 3

Tensile Strength and Modulus.

| | DRY | | WET | |
| --- | --- | --- | --- | --- |
| *Matrix (porcine) | Tensile Strength (N) | Tensile Modulus (MPa) | Tensile Strength (N) | Tensile Modulus (MPa) |
| Pleura 4-layer laminate Source 1 | — | — | 10.35 ± 3.32 | 45.79 ± 16.31 |

TABLE 3-continued

Tensile Strength and Modulus.

| *Matrix (porcine) | DRY | | WET | |
|---|---|---|---|---|
| | Tensile Strength (N) | Tensile Modulus (MPa) | Tensile Strength (N) | Tensile Modulus (MPa) |
| Pleura 8-layer laminate Source 1 | — | — | 37.21 ± 16.24 | 30.24 ± 11.24 |
| Pleura 4-layer laminate Source 2 | 64.9 ± 16.65 | 347.7 ± 97.3 | 21.11 ± 3.43 | 58.68 ± 15.18 |
| Peritoneum 4 layer laminate Source 2 | 114.9 ± 28.54 | 363.0 ± 49.4 | 34.17 ± 15.76 | 20.68 ± 6.47 |
| SIS 10-Layer laminate | 115.1 ± 5.53 | 1719.4 ± 232.8 | | |
| Dermal matrix | — | — | 140.1 ± 12.2 | 25.4 ± 0.70 |

*Source 1 was tissue from Farm to Pharm. Source 2 was Tissue Source that were the pathogen free pigs. SIS was the 10-layer product. The dermal matrix was porcine dermis.

3-Point Bending Test. The bending test measures the rigidity or stiffness of the material. The bending test measures the force required to bend the material under 3 point loading conditions. Bending modulus is used as an indication of a material's stiffness when flexed. Bending load is a load that leads to bending deformation of a material. Peak bending load is the maximum load a material can stand under bend load. Bending modulus is a material constant that represents its resistance to deformation under bending. A small value means high flexibility.

TABLE 4

3-Point Bending Test.

| | Bending Peak Load (N) | Bending Modulus (MPa) |
|---|---|---|
| Pleura 4-layer laminate (using material from Tissue Source, specified above) (dry) | 0.303 ± 0.131 | 362.6 ± 161.6 |
| Commercially available SIS 10-Layer laminate (dry) | 0.101 ± 0.007 | 1867.8 ± 395.3 |

As can be seen from Table 4, bending modulus of the inventive matrix was not more than about 363 MPa on average or not more than about 524 MPa including standard deviation, while the comparative material had a higher bending modulus.

Suture pullout test. Assesses the suture retention force for materials requiring suture attachment. A test to measure the resistance of a material to suture pullout of the material after a suture is applied to this material.

TABLE 5

Suture Pullout Test.

| | Suture Pullout (lb) |
|---|---|
| Pleura 4-layer laminate using material from Tissue Source (specified above) (dry) | 3.12 ± 1.88 |
| Pleura 4-layer laminate using material from Tissue Source (specified above) (wet) | 4.98 ± 1.061 |

Burst pressure. Was assessed by the Mullen Burst test and assesses the force required to burst the sample.

TABLE 6

Burst Strength Test (Determines the relative burst strength of a material.)

| | Burst Strength (N) | Burst Strength (psi) |
|---|---|---|
| Pleura 4-layer laminate using material from Farm to Pharm (specified above) (wet) | 35.05 ± 8.64 | 79.06 ± 19.48 |
| Pleura 8-layer laminate using material from Tissue Source (specified above) (wet) | 69.10 ± 30.75 | 155.82 ± 69.35 |

Figure 4:
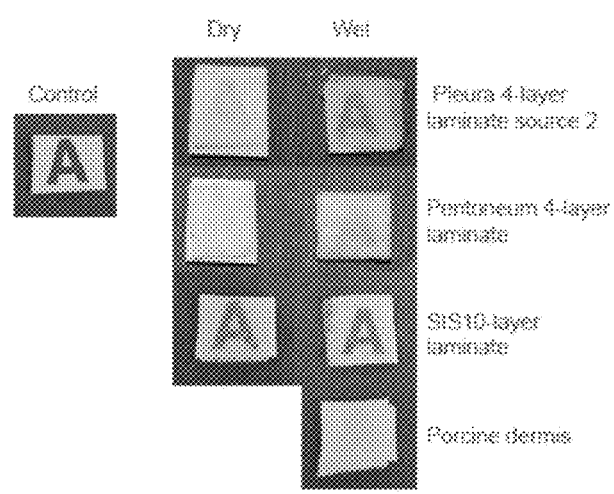
FIG. 4 illustrates the translucency of a control, 4-layer pleura laminate, a 4-layer peritoneum laminate, a commercially available 10-layer SIS (small intestinal submucosa) laminate, and a commercially available porcine dermis, which is single layer. The control was the printed Alphabet without any overlay of ECM material.
Figure 5A:
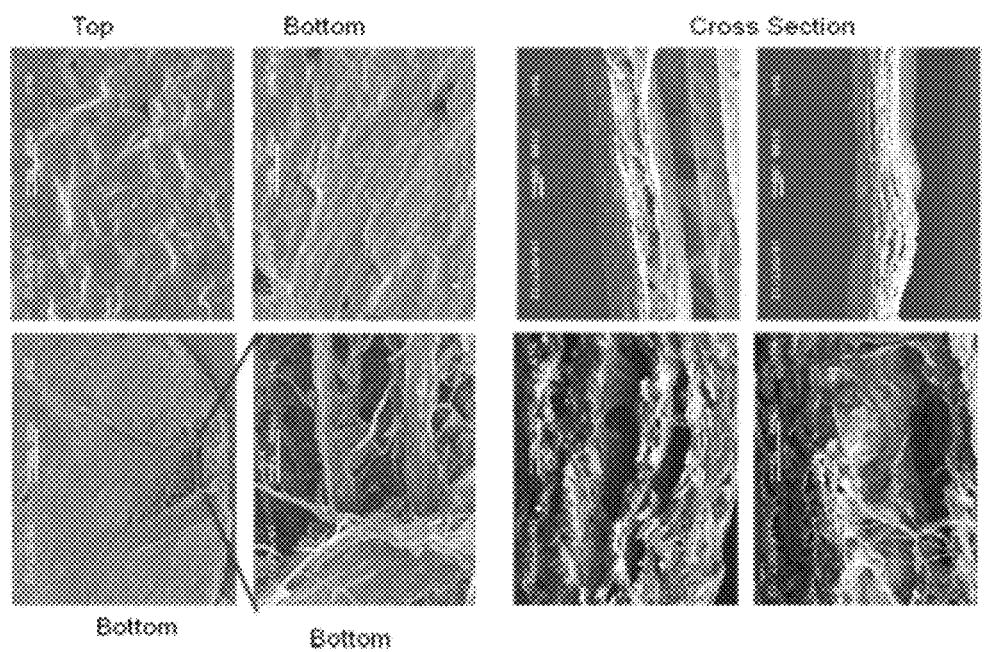
FIG. 5a is an SEM image showing the top, bottom, and cross-section views of the inventive pleural serosal-basement membrane type construct.
Figure 5B:
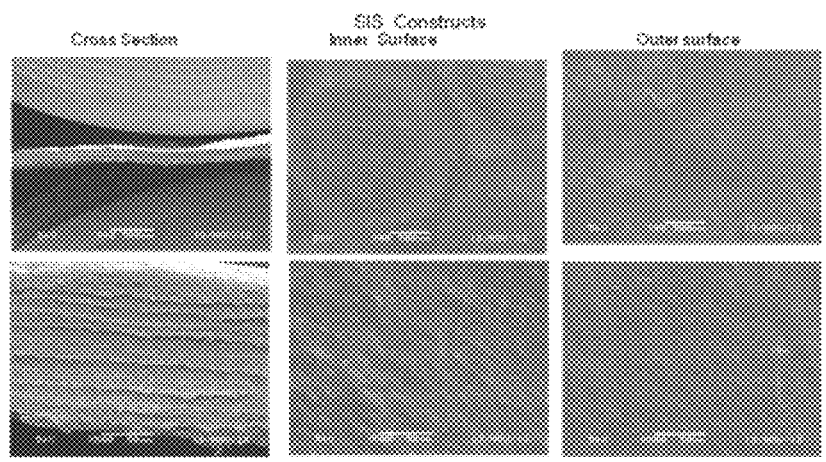
FIG. 5b is an SEM image showing the top, bottom, and cross-section views of the SIS construct.
Figure 5C:
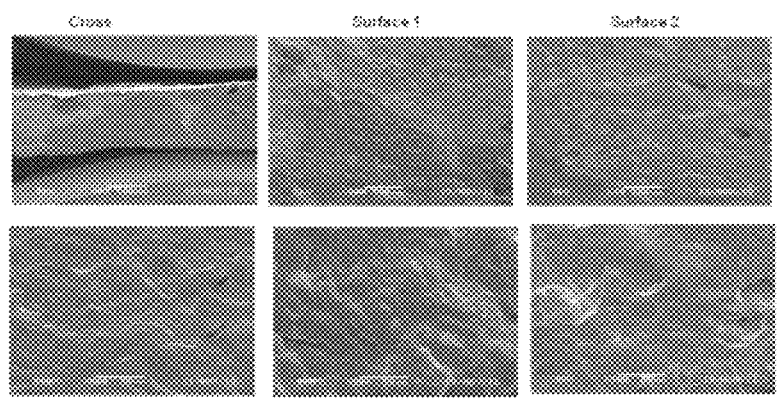
FIG. 5c is an SEM image showing the top, bottom, and cross-section views of a dermal matrix.
Figure 6:
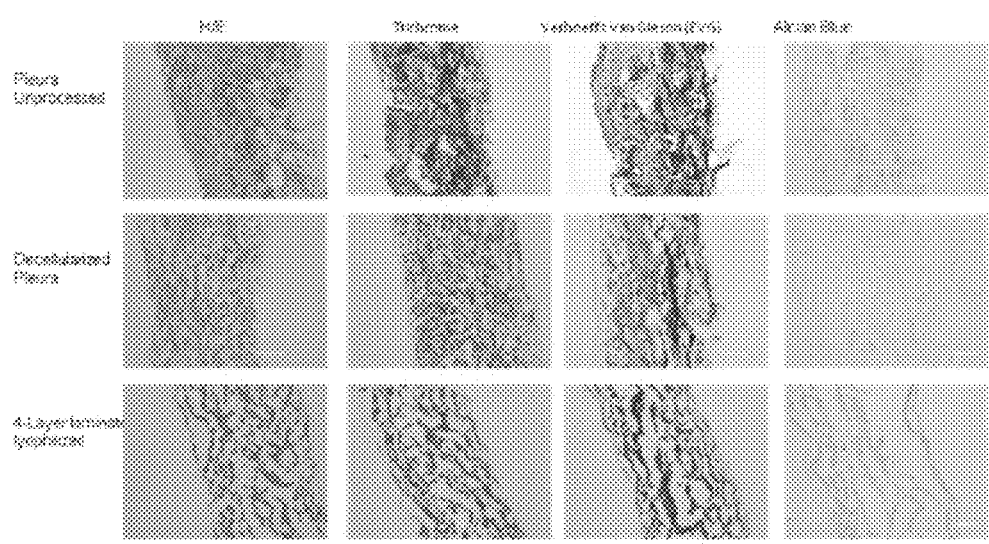
FIG. 6 is an SEM image of the inventive laminated and lyophilized pleural constructs stained with Hematoxylin and Eosin (H&E), Masson's Trichrome, Verhoeff's Van Gieson (EVG), and Alcian blue staining.
Figure 7:
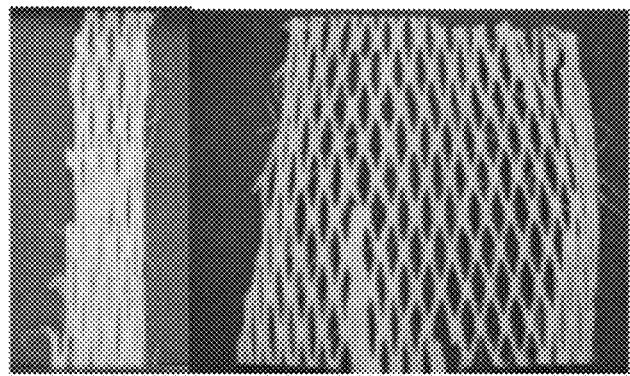
FIG. 7 illustrates a four layer laminated and lyophilized pleural construct processed through the Brennen Tissue Mesher resulting in a meshed pleura matrix.
Figure 8:
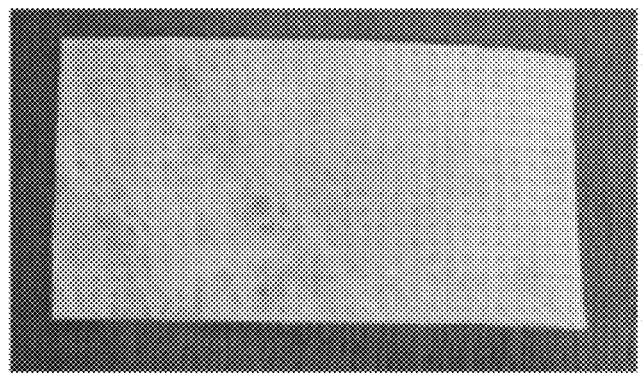
FIG. 8 illustrates a four layer laminated and lyophilized pleural construct processed by positioning between two stainless steel surfaces with blunt serrations and compressing, resulting in a texturized pleura matrix.

Translucency of the biomatrices (clinically relevant). The translucency of the biomaterials was assessed by ability to visualize an Arial 28 Points letters of English alphabet printed in Red. 1×1 cm of the biomaterials were cut and placed dry and wet (following rehydration in saline for 20 minutes). Images were captured to demonstrate the translucency of material as illustrated in FIG. 4. The control was the printed Alphabet without any overlay of ECM material.

Rehydrating speed (clinically relevant). 1×1 cm of biomaterials were cut and placed into saline and time to rehydration was assessed by stiffness to touch. 4-layer pleura laminate and 4-layer peritoneum laminate rehydrated within 3 minutes. The 10-layer SIS rehydrated after 20 minutes.

| | Pleura 4-layer laminate Source 2 | Peritoneum 4-layer laminate Source 2 | SIS 10 layer laminate |
|---|---|---|---|
| Time to rehydration | ~3 min | ~3 min | ~15-20 min |

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A biologically derived extracellular matrix (ECM) construct comprising two surfaces and a plurality of layers of decellularized pleura tissue wherein each layer of tissue has a basement membrane surface and a serosal surface wherein said ECM construct is made by a method comprising the steps of:
   providing a pleura tissue;
   decellularizing the pleura tissue;
   forming a plurality of pleura tissue layers of the decellularized pleura tissue wherein each layer of decellularized pleura tissue has a basement membrane surface and a serosal surface:
   stacking the plurality of decellularized pleura tissue layers on top of each other forming a multi-layered stack;
   compressing the multi-layered stack under vacuum;
   lyophilizing the compressed multi-layered stack; and
   optionally rehydrating the lyophilized multi-layered stack to form said decellularized ECM construct.

2. The ECM construct of claim 1, wherein the ECM has a burst strength of at least 8 N multiplied by the number of layers.

3. The ECM construct of claim 1, wherein the ECM has a tensile strength of at least 2 N multiplied by the number of layers.

4. The ECM construct of claim 1, wherein the ECM has a thickness of not more than 0.105 mm multiplied by the number of layers.

5. The ECM construct of claim 1, wherein the ECM comprises four layers of the decellularized pleura tissue and has elasticity which is characterized by a bending modulus of not more than about 363 MPa, wherein the bending modulus is measured by a 3-point bending test.

6. The ECM construct of claim 1, wherein the ECM is configured as a sheet, a perforated sheet, laminated sheets, strips, pieces, a coil, a cylinder, a weave, a vacuum pressed material, a sponge, a micronized powder, a paste, an injectable gel, a spray, an emulsion, or a coating.

7. The ECM construct of claim 1, wherein the ECM further comprises a micronized ECM deposited on at least one surface of the ECM, the micronized ECM comprising micro particles made of the decellularized pleura tissue.

8. The ECM construct of claim 1, wherein the ECM further comprises at least one layer of bioabsorbable polymers, wherein said bioabsorbable polymers are collagen, gelatin, chitosan, oxidized cellulose, oxidized regenerated cellulose, lactide-containing copolymers, glycolide containing co-polymers, or combinations thereof.

9. The ECM construct of claim 1, wherein the ECM is used to repair, reconstruct, seal, or join nervous tissue, dermal tissue, cardiovascular tissue, pericardial tissue, muscle tissue, bladder tissue, ocular tissue, periodontal tissue, bone, tendons, ligaments, pelvic floor tissue, or abdominal tissue.

10. The ECM construct of claim 1, wherein the serosal surface of at least one layer of tissue of the construct is over the serosal surface of another layer of tissue.

11. The ECM construct of claim 1, wherein the basement membrane surface of at least one layer of tissue of the construct is over the basement membrane surface of another layer of tissue.

12. The ECM construct of claim 1, wherein the serosal surface of at least one layer of tissue of the construct is over the basement membrane surface of another layer of tissue.

13. The ECM construct of claim 1, wherein the ECM construct has a serosal side and a basement membrane side.

14. The ECM construct of claim 1, wherein the ECM construct has two serosal sides.

15. The ECM construct of claim 1, wherein the ECM construct has two basement membrane sides.

16. The ECM construct of claim 1, wherein the pleura tissues is of mammalian origin.

17. The ECM construct of claim 16, wherein the pleura tissue is derived from porcine, bovine, ovine, canine, murine, simian, caprine, equine, avian, or human.

18. A method of making a biologically derived extracellular matrix (ECM) construct, comprising the steps of:
   providing a pleura tissue;
   decellularizing the pleura tissue;
   forming a plurality of pleura tissue layers of the decellularized pleura tissue wherein each layer of decellularized pleura tissue has a basement membrane surface and a serosal surface:
   stacking the plurality of decellularized pleura tissue layers on top of each other forming a multi-layered stack;
   compressing the multi-layered stack under vacuum;
   lyophilizing the compressed multi-layered stack; and
   optionally rehydrating the lyophilized multi-layered stack to form said decellularized ECM construct.

19. The method of claim 18 wherein the compressed multi-layered stack has a serosal side and a basement side.

20. The method of claim 18 wherein the compressed multi-layered stack has two serosal sides.

21. The method of claim 18 wherein the compressed multi-layered stack has two basement membrane sides.

22. The method of claim 18 wherein the serosal surface of at least one layer of decellularized pleura tissue of the construct is stacked over the serosal surface of another layer of decellularized pleura tissue.

23. The method of claim 18 wherein the basement membrane surface of at least one layer of decellularized pleura tissue of the construct is over the basement membrane surface of another layer of decellularized pleura tissue.

24. The method of claim 18 wherein the serosal surface of at least one layer of decellularized pleura tissue of the construct is over the basement membrane surface of another layer of decellularized pleura tissue.

* * * * *